United States Patent
Kaiser

(10) Patent No.: US 11,788,048 B2
(45) Date of Patent: Oct. 17, 2023

(54) SYSTEMS AND METHODS FOR A COLLAPSIBLE CHAMBER WITH FOLDABLE MIXING ELEMENT

(71) Applicant: Life Technologies Corporation, Carlsbad, CA (US)

(72) Inventor: Stephan Kaiser, San Jose, CA (US)

(73) Assignee: Life Technologies Corporation, Carlsbad, CA (US)

( * ) Notice: Subject to any disclaimer, the term of this patent is extended or adjusted under 35 U.S.C. 154(b) by 521 days.

(21) Appl. No.: 16/646,804

(22) PCT Filed: Sep. 14, 2018

(86) PCT No.: PCT/US2018/051070
§ 371 (c)(1),
(2) Date: Mar. 12, 2020

(87) PCT Pub. No.: WO2019/060218
PCT Pub. Date: Mar. 28, 2019

(65) Prior Publication Data
US 2020/0255784 A1 Aug. 13, 2020

Related U.S. Application Data

(60) Provisional application No. 62/560,246, filed on Sep. 19, 2017.

(51) Int. Cl.
*B01F 27/00* (2022.01)
*C12M 1/06* (2006.01)
(Continued)

(52) U.S. Cl.
CPC ........... *C12M 27/02* (2013.01); *B01F 27/054* (2022.01); *B01F 27/0727* (2022.01);
(Continued)

(58) Field of Classification Search
CPC .............. B01F 2101/44; B01F 27/054; B01F 27/0727; B01F 27/11251; B01F 27/2124;
(Continued)

(56) References Cited

U.S. PATENT DOCUMENTS

| 4,083,653 A | 4/1978 | Stiffler | |
|---|---|---|---|
| 4,289,854 A * | 9/1981 | Tolbert | B01F 33/453 435/297.1 |
| 4,639,422 A * | 1/1987 | Geimer | C12M 29/04 435/297.3 |
| 5,897,012 A * | 4/1999 | Sortwell | B65D 19/12 220/666 |

(Continued)

FOREIGN PATENT DOCUMENTS

WO 2013/151733 A1 10/2013

OTHER PUBLICATIONS

International Search Report dated Feb. 4, 2019, issued in PCT Application No. PCT/US2018/051070, filed Sep. 14, 2018.
Written Opinion dated Feb. 4, 2019, issued in PCT Application No. PCT/US2018/051070, filed Sep. 14, 2018.

*Primary Examiner* — Anshu Bhatia
(74) *Attorney, Agent, or Firm* — Mintz, Levin, Cohn, Ferris, Glovsky and Popeo, P.C.

(57) ABSTRACT

The present set of embodiments relate to a system, method, and apparatus for culturing cells within a cell culture vessel having a mixing element. The cell culture system includes a flexible portion and a mixing element disposed therein. The mixing element includes a suspended foldable portion. The system is configured to reduce shear stress on cells without compromising mixing efficiency. This reduction is accomplished by using a mixing element having a large surface area allowing for reduced rotational speeds. The system is collapsible for ease of transport and disposal. The flexible portion collapses and the foldable portion folds to minimize the volume of the system while not in operation.

17 Claims, 19 Drawing Sheets

(51) Int. Cl.
*C12M 1/00* (2006.01)
*B01F 27/054* (2022.01)
*B01F 27/072* (2022.01)
*B01F 27/2124* (2022.01)
*B01F 27/1125* (2022.01)
*B01F 35/513* (2022.01)
*B01F 101/44* (2022.01)

(52) U.S. Cl.
CPC .... *B01F 27/11251* (2022.01); *B01F 27/2124* (2022.01); *B01F 35/513* (2022.01); *C12M 23/26* (2013.01); *B01F 2101/44* (2022.01)

(58) Field of Classification Search
CPC ...... B01F 35/513; C12M 23/14; C12M 23/26; C12M 27/02
See application file for complete search history.

(56) References Cited

U.S. PATENT DOCUMENTS

| | | |
|---|---|---|
| 6,769,800 B1 * | 8/2004 | Young .................. B01F 35/55 366/307 |
| 8,192,071 B2 | 6/2012 | Wright et al. |
| 9,540,606 B2 | 1/2017 | Kunas et al. |
| 2005/0272146 A1 | 12/2005 | Hodge et al. |
| 2011/0229963 A1 * | 9/2011 | Fatherazi ............ B01F 35/513 366/343 |
| 2015/0117142 A1 * | 4/2015 | Staheli ................ B01F 27/191 366/279 |
| 2015/0265988 A1 * | 9/2015 | Williams ........... B01F 35/4111 366/204 |
| 2017/0183617 A1 | 6/2017 | Jones et al. |
| 2019/0345433 A1 * | 11/2019 | Prabhudharwadkar ...................... C12M 27/02 |

\* cited by examiner

SYSTEMS AND METHODS FOR A COLLAPSIBLE CHAMBER WITH FOLDABLE MIXING ELEMENT

CROSS REFERENCE TO RELATED APPLICATIONS

This application claims priority to PCT/US2018/051070, filed on Sep. 14, 2018, which claims priority to U.S. application No. 62/560,246 filed Sep. 19, 2017, which disclosures are herein incorporated by reference in its entirety.

FIELD OF THE INVENTION

The present disclosure generally relates to bioproduction and more particularly to systems, apparatuses, and methods for cell culture or fermentation.

BACKGROUND

In the biopharmaceutical industry bacteria, fungi, animal cells, insect cells, and plant cells have been used for the production of recombinant proteins, antibodies, and vaccines. These unicellular microorganisms are often sensitive to both non-biological (e.g., temperature, pH value, hydrodynamics, etc.) and biological factors (e.g., metabolite concentrations, growth factors, etc.). Such microorganisms may be cultivated in fermenters or bioreactors which may provide a well-controlled, contaminant-free environment for the desired biological reaction.

Stainless steel tanks have been traditionally used for cell cultivation. Steel tanks require cleaning and sterilization in order to achieve a sterile environment. The required bioreactor and maintenance equipment results in a large laboratory footprint which is associated with high installation and maintenance costs. Over the last two decades, an increasing number of single-use bioreactors have been developed and implemented for use in the biopharmaceutical industry. In contrast to their conventional counterparts, single-use bioreactors may be made of plastic materials, arrive pre-assembled, come pre-sterilized by beta or gamma irradiation, and may be supplied ready-to-use by the manufacturers. Typically plastic materials may be used for the construction of the single-use vessels or at least the innermost layer being in contact with the aqueous culture medium. The cultivation containers may be discarded after a single use. Consequently, cleaning and sterilization may be reduced or eliminated and the risk of cross contaminations is also reduced.

The existing single-use bioreactors differ in geometry, mixing principle, and instrumentation. For laboratory scale applications, single-use cultivation vessels often comprise a rigid, hard shell tank, whereas flexible liner bags are typically used for pilot and production systems. The liner bags, which may be either two-dimensional ("pillow"-like) or three-dimensional in shape, may be made of multi-layer films that may comprise LDPE or EVA for at least their inner layer. Three-dimensional bags are fixed and shaped by rigid glass or stainless steel containers that may incorporate water filled double jackets for heating and cooling of the bioreactor bags.

Although a number of different systems have been introduced to the market place, mechanically agitated single-use bioreactors are most common in industrial applications. Prior art wave-mixed bioreactors typically have two-dimensional bags that are partially filled, as shown in FIG. 1. The rocking motion of a platform on which the culture bag is placed introduces a wave motion inside the bag. The wave characteristics depend on the bag geometry, the rocking angle and rate, the filling level, as well as the liquid properties (i.e., density and viscosity). While wave-mixed bioreactors have proven to be suitable for seed-train and small to medium scale production, their size is limited due to mechanical constraints of the pillow bags and the rocker platform as well as a relatively large footprint.

In addition to the wave-mixed rocker type bioreactors, an orbital motion may also be used to agitate a bioreactor, as shown in FIG. 2. Similar to the rocker type systems, these bioreactors are relatively easy and cheap to manufacture, but mixing and oxygen mass transfer may become limiting, in particular at larger scales, due to the low specific interface surface area (i.e., free surface to volume ratio). Furthermore, the bioreactor container is often shaken along with the bioreactor holder and consequently a larger mass has to be moved, resulting in higher power demands.

Most stirred bioreactors are agitated by single or multi-stage impellers which are mounted near the tank bottom or on a central shaft as shown in FIG. 3. However, the energy dissipation into the liquid is often inhomogeneous due to the small swept volume of the impellers (i.e., the region swept by the rotating impeller). Consequently, high agitation speeds are required to effectively mix the vessel content which may increase the hydrodynamic or shear stress to the culture broth and cells contained therein. Hydrodynamic or shear stress may result in cellular damage and decreased productivity, particularly, for shear sensitive cultures. The use of multiple impellers, as shown in FIG. 4, mimics conventional mixing tanks more closely, but may confer several disadvantages. In particular, drive shafts that penetrate the bag wall must be sealed to prevent contamination. Manufacturing these kinds of bags may be complicated and expensive while also requiring more storage space. Additionally, rigid impellers may damage the bags.

In summary, bioreactors in the current market may suffer from limited scalability, low turn-down ratios, inefficient mixing due to small swept volumes, cellular shearing, low oxygen mass transfer capacities, large packaging sizes for the cultivation bags, and large laboratory footprints.

In fields that require mixing systems or in the field of bioproduction, improvements are desired to solve the described issues.

BRIEF SUMMARY OF THE INVENTION

In one aspect, a collapsible cell culture vessel and system is disclosed. The cell culture system may include a flexible portion adapted to support a cell culture and a mixing element comprising a foldable portion disposed within the flexible portion for mixing the cell culture. The cell culture vessel may include cells and nutrients to support cellular growth. The flexible portion of the cell culture system may be configured to collapse to about 15%, about 10%, about 5%, about 10% to about 20%, about 5% to about 25%, about 5% to about 10%, about 15% to about 20%, or about 20% to about 25% of its operational configuration. The flexible portion may comprise an elliptical, circular or polygonal cross-section. The flexible portion may include at least three panels wherein the panels may be joined by a seam. The seam may include a weld or a fold. The foldable portion may fold substantially flat when the flexible portion is collapsed. The foldable portion may comprise a polymeric sheet and the polymeric sheet may comprise a single polymer or multiple polymeric layers. The multiple polymeric layers may comprise different compositions wherein the polymeric layer contacting the cell culture may be selected to minimize leaching. The foldable portion may be substantially rectangular. The foldable portion may comprise two foldable portions, three foldable portions, or four foldable portions. The foldable portion may include an opening wherein the opening may be a slit. The opening may be configured to direct a fluid flow path. The foldable portion may include a surface feature wherein the surface feature may comprise a protrusion. The protrusion may include a rod, cone, or dimple. The surface feature may comprise a rib or a contour for directing fluid flow. The surface feature may comprise an object embedded within the foldable portion. The surface feature may be configured to pack adjacent to a second surface feature. The surface feature may include a flap. A section or portion of the foldable portion may remain above a fluid level while the vessel or system is in operation. The flexible portion may have a first height and the foldable portion may have a second height wherein the ratio of the second height to the first height is about 0.5 to about 1.0, about 0.7 to about 0.95, about 0.8 to about 0.9, about 0.8, about 0.9, or about 0.95. The mixing element may further comprise a suspension element wherein the suspension element may further comprise a hub and an arm extending from the hub. The arm may comprise an elliptical cross-section and may be straight, curved, or angled. The hub may comprise a portion that is in physical communication to the exterior of the flexible portion through a rotor assembly. The suspension element may be three dimensionally printed or molded. The arm may be welded or adhered to the hub and may include a contact layer. The suspension element may further include a polymer or a hollow portion. The suspension element may include a reinforcing metal or stainless steel component. The arm may be configured to telescope between two or more lengths. In addition to the suspension element, the mixing element may comprise an opposing suspension element wherein the foldable portion may be suspended between the suspension elements. Each suspension element may comprise an arm and a hub. The suspension elements may be misaligned to create a lagging portion of the foldable portion. The arms of the opposing suspension elements may be different lengths or the same length. The hubs of the opposing suspension elements may have differing rotational axes or a common rotational axis, as shown in FIG. 9. The mixing element may comprise a securing element wherein the securing element joins the foldable portion and the suspension element. The securing element may comprise a weld, an adhesive, or a mechanical element. The flexible portion may comprise a rotor assembly affixed thereto wherein the rotor assembly may comprise a housing and the housing may be affixed to the flexible portion with a weld. The rotor assembly may further comprise a seal, a ball bearing, a washer, and a snap ring. The rotor assembly may interact with a drive. The rotor assembly may comprise a positioning cage and two opposing magnets associated with the positioning cage. The two opposing magnets may reside on the exterior of the flexible portion. The rotor assembly may be disposed within the flexible portion in its entirety. The flexible portion may further include a sterile gas inlet including a filter element. The flexible portion may further comprise a gas outlet. The flexible portion may include an aerator wherein the aerator may include a sparger. The flexible portion may include a port wherein the port may comprise a sampling port, sensor port, or tube port. The flexible portion may include a baffle. The mixing element may be configured to aerate the cell culture.

In one aspect, a mixing system for reducing cellular shear stress is disclosed. The mixing system may comprise a flexible portion and a mixing element comprising a foldable portion disposed within the flexible portion, wherein the foldable portion has a sweep area ratio optimized to reduce shear stress. The foldable portion may comprise a polymeric sheet. The sweep area ratio may comprise a largest cross sectional area of the foldable portion divided by a largest cross sectional area of the flexible portion wherein the sweep ratio may be about 0.25 to about 1.0, about 0.5 to about 1.0, about 0.75 to about 1.0, about 0.25 to about 0.35, about 0.35 to about 0.45, about 0.45 to about 0.55, about 0.55 to about 0.65, about 0.65 to about 0.75, about 0.75 to about 0.85, about 0.85 to about 0.96, or about 0.95 to about 1.0.

In one aspect, a mixing system for varying volumetric ranges is disclosed. The mixing system may comprise a flexible portion having a surface and a mixing element comprising a foldable portion disposed within the flexible portion wherein a space between the surface and the foldable portion determines a minimal working volume. The foldable portion may comprise a polymeric sheet material. The space of the mixing system may be about 1% to about 20%, about 5% to about 15%, about 7% to about 12%, about 1% to about 5%, about 5% to about 10%, about 10% to about 15%, or about 15% to about 20% of the total volume of the flexible portion.

In one aspect, a collapsible cell culture vessel is disclosed. The vessel may comprise a flexible portion adapted to support a cell culture and a mixing element comprising a foldable portion disposed within the flexible portion for mixing the cell culture, wherein the foldable portion may include a fold. The foldable portion may include a polymeric sheet material. The fold may include an angle between about 0 degrees and about 179 degrees, about 0 to about 90 degrees, about 0 to about 80 degrees, about 0 to about 70 degrees, about 0 to about 60 degrees, about 0 to about 50 degrees, about 0 to about 40 degrees, about 0 to about 30 degrees, about 0 to about 20 degrees, about 0 to about 10 degrees, or about 0 to about 5 degrees.

In one aspect, a method of culturing cells using a collapsible cell culture vessel is disclosed. The method may include providing a flexible portion containing a culture media with nutrients that support in vitro cultivation of cells. The method may include providing a mixing element disposed within the flexible portion to mix a cell culture, wherein the mixing element comprises a foldable portion. The method may include inflating the flexible portion. The method may include unfolding the foldable portion. The foldable portion may include a polymeric sheet material. The method may include adding cells to the cell culture. The method may include culturing the cells. The method may include harvesting a component of the cell culture. The method may include the step of mixing the fluid comprising a cell culture using the mixing element. The method may include the step of collapsing the flexible portion to about 15%, about 10%, about 5%, about 10% to about 20%, about 5% to about 25%, about 5% to about 10%, about 15% to about 20%, or about 20% to about 25% of its operational configuration.

In one aspect, a method to reduce cellular shear stress is disclosed. The method may comprise providing a flexible portion having a mixing element comprising a foldable portion, wherein the foldable portion has a sweep area ratio and may comprising mixing fluid containing a cell culture using the mixing element. The foldable portion may comprise a polymeric sheet material. The sweep ratio may comprise a largest cross sectional area of the foldable portion divided by a largest cross sectional area of the flexible portion. The method may include a sweep area ratio of about 0.25 to about 1.0, 0.5 to about 1.0, 0.75 to about 1.0, about 0.25 to about 0.35, 0.35 to about 0.45, about 0.45 to about 0.55, about 0.55 to about 0.65, about 0.65 to about 0.75, about 0.75 to about 0.85, about 0.85 to about 0.95, or about 0.95 to about 1.0.

BRIEF DESCRIPTION OF THE DRAWINGS

The novel features of the various embodiments are set forth with particularity in the appended claims A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Embodiments of systems, methods, and apparatuses for cell culture are described in the accompanying description and figures. In the figures, numerous specific details are set forth to provide a thorough understanding of certain embodiments. A skilled artisan will be able to appreciate that the cell culture system described herein may be used for a variety of applications including, but not limited to, cell culture and fermentation. Additionally, the skilled artisan will appreciate that certain embodiments may be practiced without these specific details. Furthermore, one skilled in the art will readily appreciate that the specific sequences in which methods are presented and performed are illustrative and it is contemplated that the sequences may be varied and still remain within the spirit and scope of certain embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Furthermore, in described various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art will readily appreciate that the sequence may be varied and still remain within the spirit and scope of the various embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Figure 5:
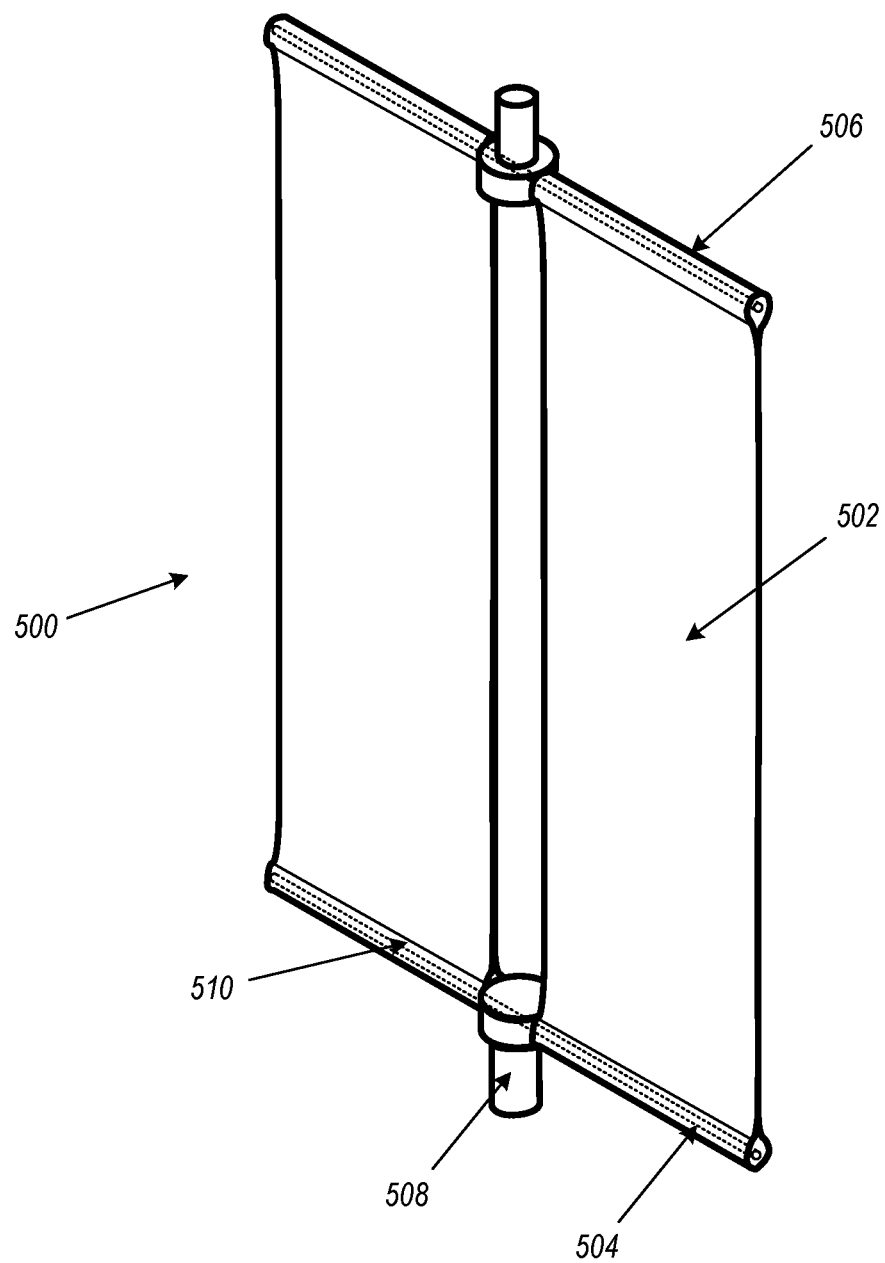
FIG. 5 illustrates a perspective view of an exemplary mixing element according to one of the various embodiments.

FIG. 5 is an illustration of an embodiment of a mixing element 500 for use in a cell culture system. Various embodiments may include a foldable portion 502 suspended between first and second suspension elements 504, 506 and one or more hubs 508 having one or more arms 510 extending therefrom.

In various embodiments, a mixing element 500 may be configured to both mix the contents of a cell culture as well as aerate the cell culture by introducing gas into the fluid or liquid. The hub 508 may be configured to rotate which may allow the foldable portion 502 to sweep through the cell culture and, thereby, mix and aerate a cell culture or suspension. In various embodiments, the foldable portion 502 may be configured for gentle mixing which may be appropriate for various applications including adherent cell cultures. In various embodiments, the foldable portion 502 may include a polymeric sheet that may comprise a single layer or multiple layers. In the embodiments including a multi-layered polymeric sheet, the layers may either be of the same composition or of different compositions. For example, in various embodiments an innermost layer may be selected based on leaching properties. Specifically, some cell culture applications may require the innermost layer (i.e., The layer contacting the culture.) to have very low or no leaching.

Figure 6:
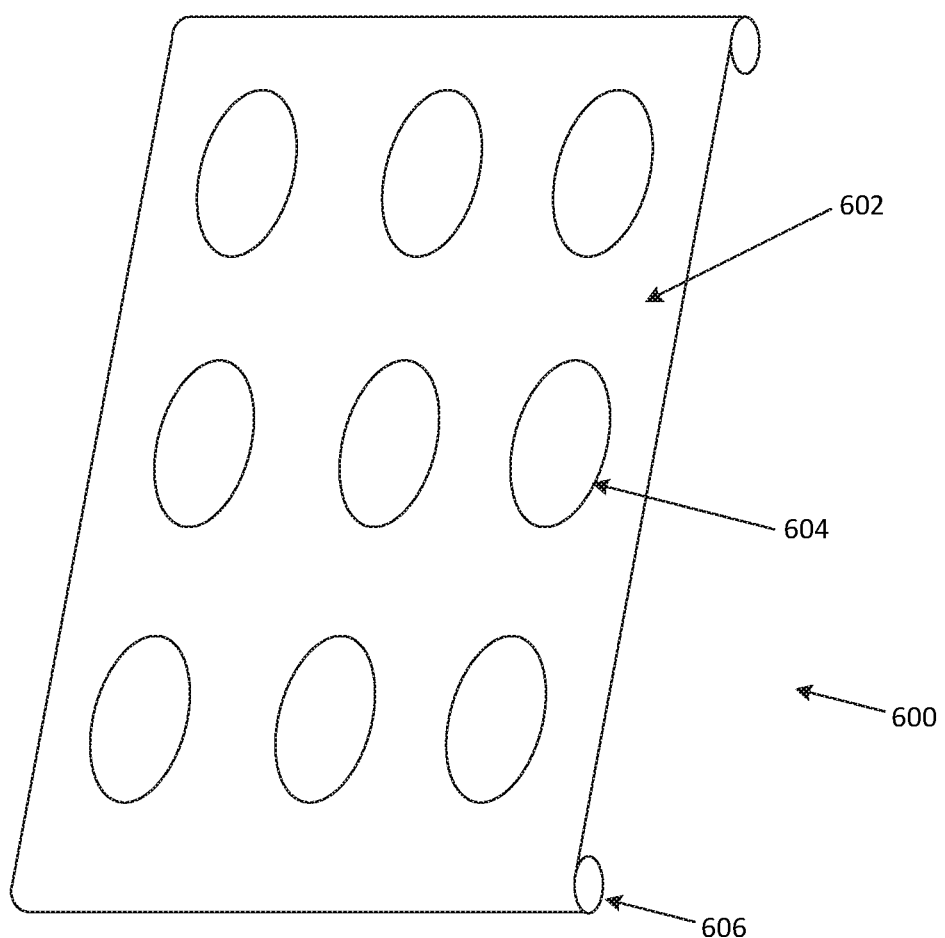
FIG. 6 illustrates a perspective view of another exemplary mixing element according to one of the various embodiments.

FIG. 6 is an illustration of an embodiment of a mixing element 600 comprising a foldable portion 602 having openings 604 and one or more securing elements 606. In various embodiments, the openings 604 may be slits configured to direct fluid flow. In other embodiments, the openings may be any shape, including, but not limited to, elliptical or polygonal. In embodiments having two or more foldable portions 602, the openings 604 for each of the foldable portions 602 may either be aligned or misaligned.

Figure 7:
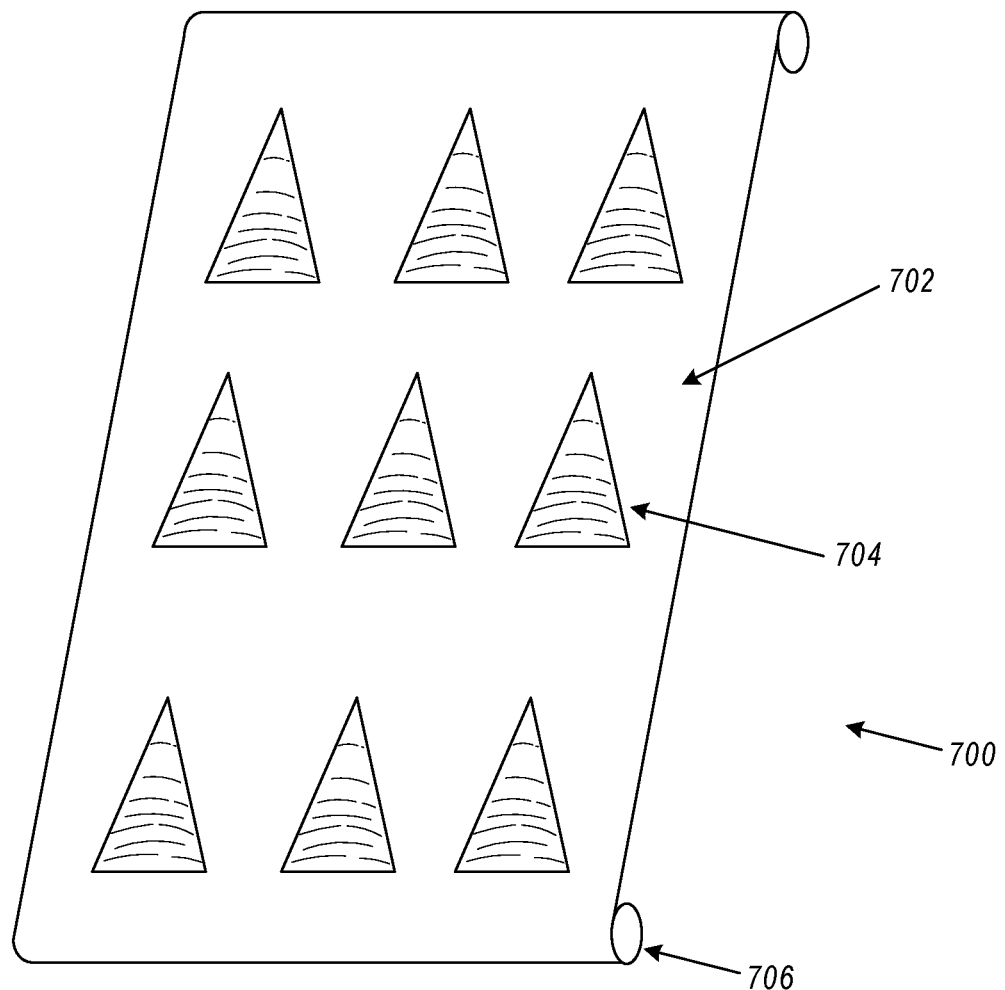
FIG. 7 illustrates a perspective view of another exemplary mixing element according to one of the various embodiments.

FIG. 7 is an illustration of an embodiment of a mixing element 700 comprising a foldable portion 702 having surface features 704 and a securing element 706. In various embodiments, the surface feature 704 may include protrusions, rods, cones, dimples, ribs, contours, or objects embedded within the foldable portion 702 to create the surface feature 704. In some embodiments, the surface feature 704 may be configured to direct fluid flow in a manner that creates a more vigorous or turbulent flow. Fluid flow direction may be facilitated by surface features 704 acting as or creating channels on the foldable portion. In some embodiments, more than one surface feature 704 may be configured pack adjacent to one another in a tightly packed formation to minimize the volume of a cell culture system in a collapsed state (see FIG. 11). In other embodiments, the surface features 704 may be designed to self-organize for ease of collapsing the cell culture system. In some embodiments, the rib or contour may have a shape that may be straight, curved, or angled depending on the mixing and aeration properties needed for a given application.

In various embodiments, the surface feature 704 may be attached to the foldable portion 702 using a weld, adhesive, or mechanical attachment. A mechanical attachment may include a pin, screw, or any other known means of mechanical securing. In some embodiments, the surface feature 704 may be part of the same polymer as the foldable portion 702. In embodiments where the surface feature 704 is created by embedding an object within the foldable portion 702, the object may be a polymeric bead or any other object capable of creating a bump or protrusion. In some embodiments, the embedded object may reside between the two or more polymeric layers used to create the foldable portion 702. In other embodiments, the surface feature may include a flap with a portion trailing the foldable portion 702. In some embodiments, the flap may include a polymeric sheet and may also include protrusions, rods, cones, dimples, ribs, contours, or objects embedded within the flap.

Figure 8:
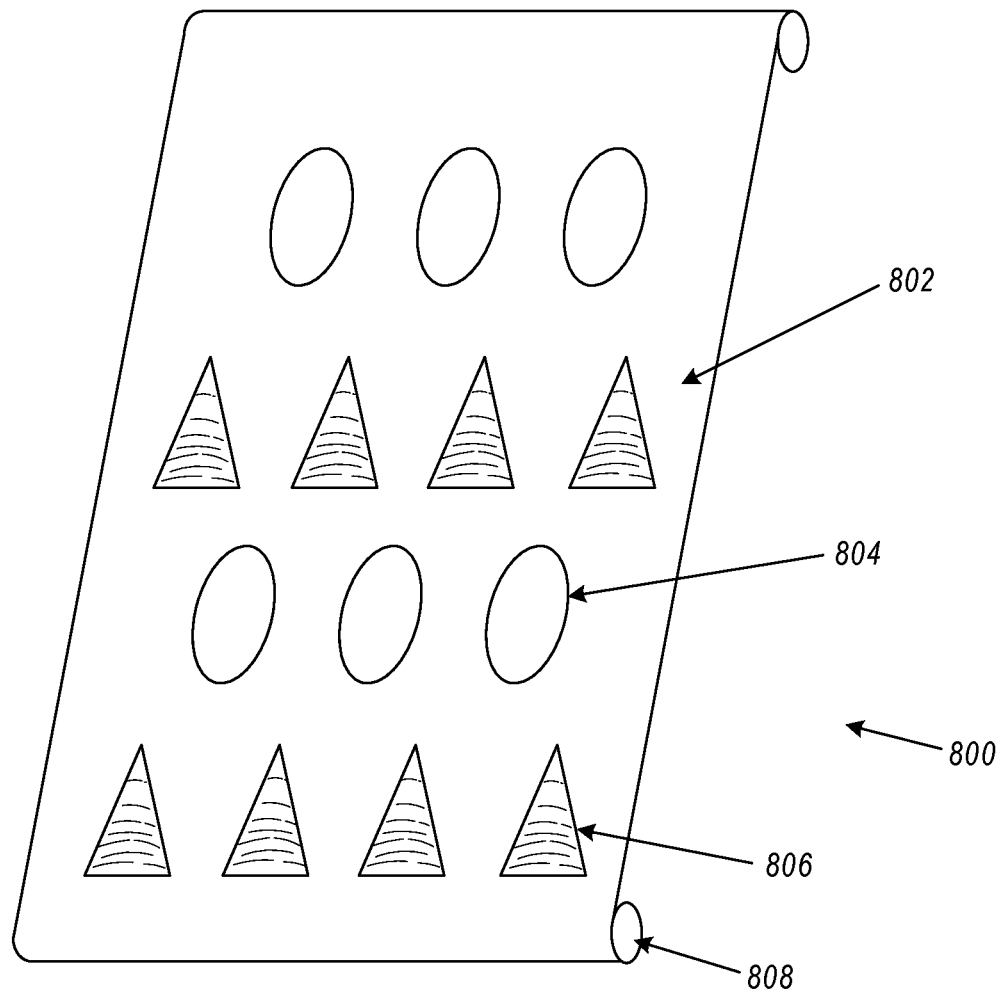
FIG. 8 illustrates a perspective view of another exemplary mixing element according to one of the various embodiments.

FIG. 8 is an illustration of an embodiment of a mixing element 800 comprising a foldable portion 802, both openings 804 and surfaces features 806, and a securing element 808. In various embodiments, having a foldable portion 802 with both openings 804 and surfaces features 806 may be necessary to optimize the amount of turbulent flow for a given cell culture.

Figures 9A, 9B, 9C:
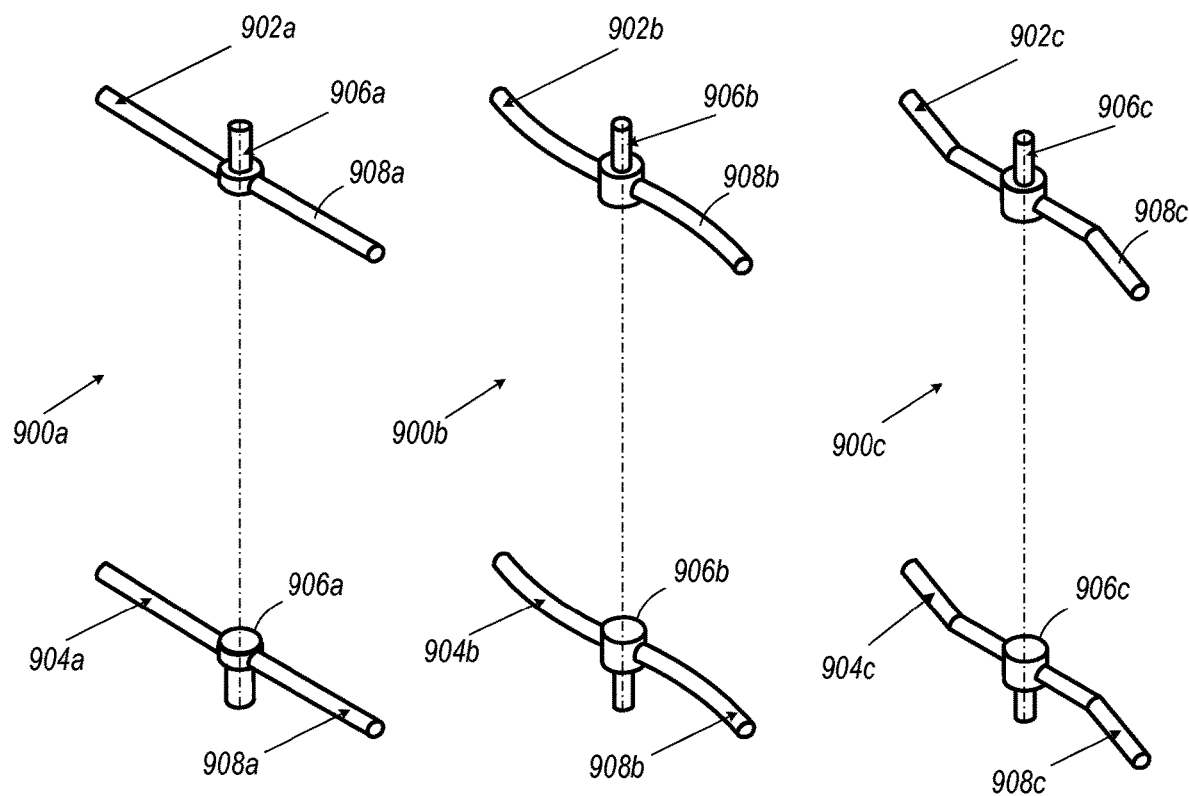
FIGS. 9A, 9B, and 9C illustrate perspective views of exemplary mixing elements according to various embodiments.

FIGS. 9A, 9B, and 9C illustrate embodiments of mixing elements comprising first and second suspension elements 902A, 902B, 902C, 904A, 904B, 904C, hubs 906A, 906B, 906C, with arms 908A, 908B, 908C attached thereto. In various embodiments, suspension elements 902, 904 may include hubs 906A, 906B, 906C that may be in physical communication with arms 908A, 908B, 908C. In various embodiments, the suspension elements may comprise a polymer with a contact layer selected to reduce leeching into the cell culture.

In various embodiments, at least one arm 908 may extend from at least one hub 906. In some embodiments, the arm 908 and hub 906 may be a single molded or three dimensionally printed piece. In other embodiments, the arm 908 and hub 906 may be connected to one another with a weld or using thermal fusion, adhesive, or mechanical attachment device such as a pin, screw, or any other known means of mechanical securing. In various embodiments, the mechanical attachment device may include snap-fit joints.

In various embodiments, each of the one or more arms may include an elliptical, circular, oval, rectangular, or polygonal cross-section. In some embodiments, the arms 908 may be straight 908A, curved 908B, or angled 908C depending on the cell culture application. As illustrated in FIGS. 9A, 9B, and 9C the upper arms 908 and the lower arms 908 are aligned along the same plane, however, there may be some applications where a misalignment, creating a lagging foldable portion, may be utilized to increase or decrease turbulent mixing. In other embodiments, at least one arm 908 may be configured to telescope between various lengths. In some embodiments, the shape of the foldable portion may include a trapezoid, kite, or parallelogram configuration and relate to the size and length of the arms 908.

In various embodiments, the arms 908 may be hollow to reduce weight or reinforced with some other kind of material that may include a metal such as stainless steel or a dense polymer.

In various embodiments, the foldable portions 602, 702, 802 illustrated in FIGS. 6, 7, and 8 may be secured using a securing element 606, 706, 808 to arms 908 as illustrated in FIG. 9. The purpose of a securing element may be to join a foldable portion 602, 702, 802 to an arm 908 using a bond, weld, adhesive, or mechanical attachment. A mechanical attachment may include a rivet, pin, screw, or any other known means of mechanical securing. In other embodiments, the foldable portion may wrap around at least one arm 908 and be bonded, welded, or adhered to itself.

In various embodiments, the corresponding hubs 906 may be aligned in order to be on the same rotational axis or, in other embodiments, may be misaligned to alter the aeration and mixing properties of the mixing element 900.

Figure 10:
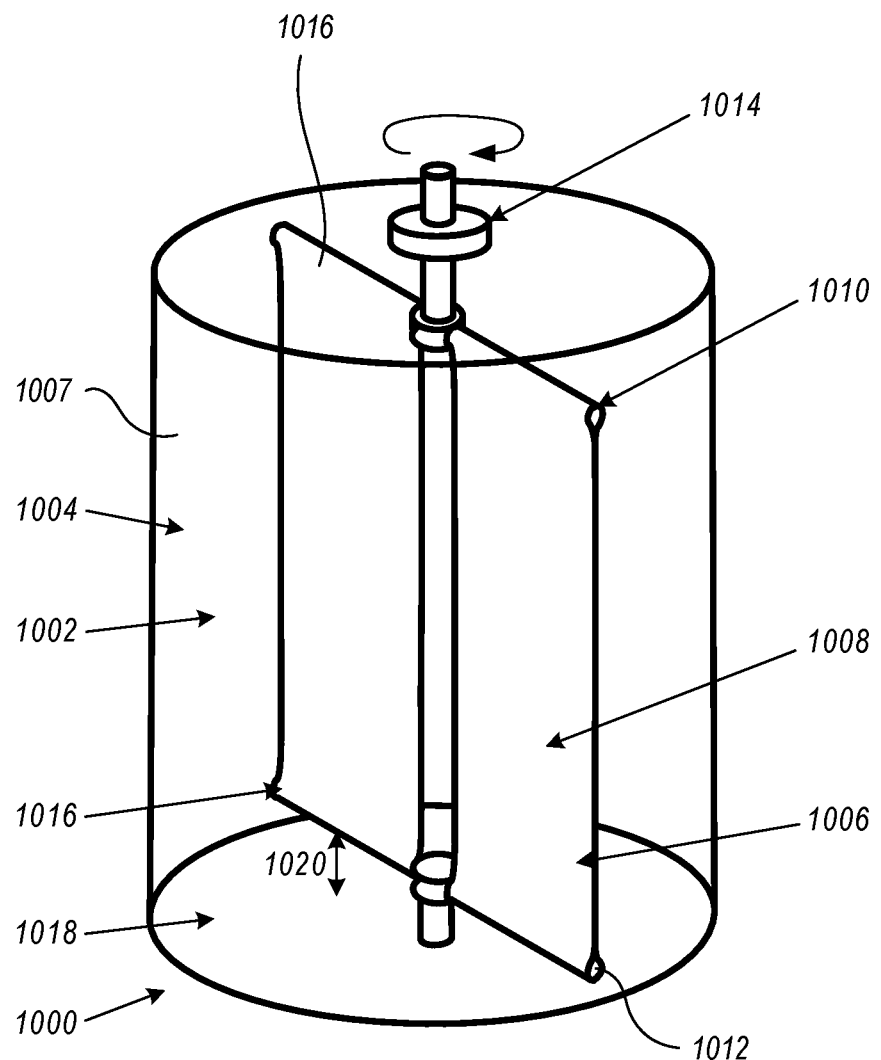
FIG. 10 illustrates a perspective view of an exemplary cell culture system according to one of the various embodiments.

FIG. 10 is an illustration of an embodiment of a cell culture system 1000 comprising a flexible portion 1002 being comprised of a flexible material 1004 and having a surface 1008. In the depicted embodiment, flexible portion 1002 can comprise a collapsible container bounding a chamber 1007. The flexible portion 1002 further comprises a mixing element 1006 therein including a foldable portion 1008, first and second suspension elements 1010, 1012, at least one hub 1014, and at least one arm 1016. In various embodiments, there is a space 1020 between the surface 1018 and an arm 1016 in order to enable free rotation of the mixing elements. In some embodiments, the space 1020 may determine the turn-down ratio. In various embodiments, the flexible portion 1002 has a circular or an elliptical cross section. In various embodiments, the interior of the flexible portion 1002 coming into contact with a cell culture may have surface features including protrusions, rods, cones, dimples, ribs, contours, or objects embedded within the flexible material 1004 to achieve desired aeration and mixing properties. Depending on the application those properties may include more or less turbulent flow or more or less laminar flow. In various embodiments, any or all of the components within the cell culture system may comprise materials that are resistant to sterilization radiation. In various embodiments, any of the above mentioned components may be constructed from polyethylene, polypropylene, polycarbonate, polyesters, ethylene vinyl alcohol or any combination thereof. In some embodiments, the entire cell culture system 1000 may reside within a rigid housing.

In various embodiments, the mixing element 1006 may be disposed within the flexible portion 1002 and may be configured to rotate within the flexible portion 1002. The rotational movement may be driven through a hub 1014 where a portion of the hub may be exposed to the exterior of the flexible portion through a sterile interface. Through transfer of power from the hub 1014 to the suspension elements 1010, 1012 to drive the foldable portion 1008 in a roughly circular path through the flexible portion 1002 a cell culture may be mixed and aerated. As depicted in FIG. 10, in one exemplary embodiment, suspension elements 1010 and 1012 can be spaced apart within chamber 1007 so that there is no direct or indirect connection between suspension elements 1010 and 1012 within chamber 1007 except through one or more of foldable portions 1008.

In various embodiments, the flexible portion 1002 may be a chamber, a collapsible chamber, container, culture vessel, or any other device capable of holding a liquid or cell culture.

Figure 11:
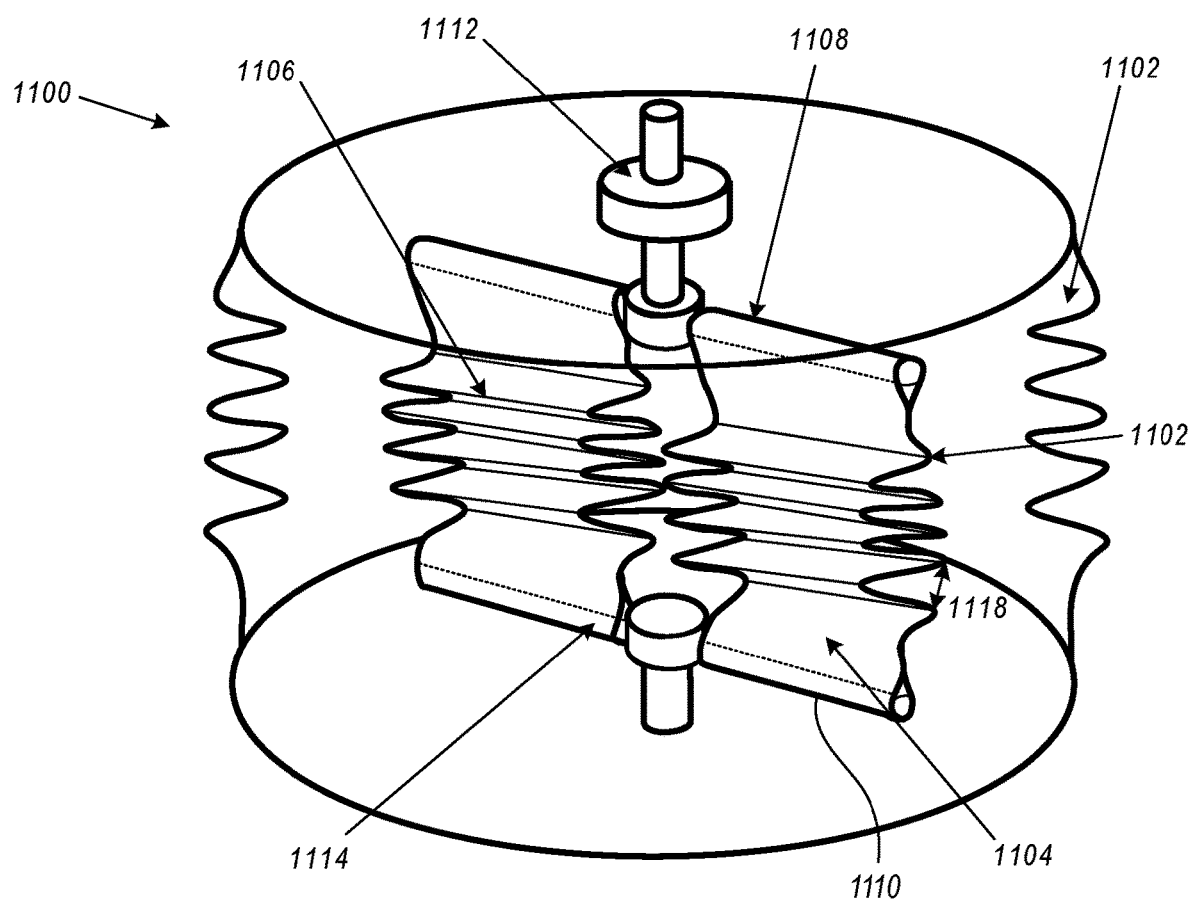
FIG. 11 illustrates a perspective view of another exemplary cell culture system in a collapsed configuration according to one of the various embodiments.

FIG. 11 is an illustration of and embodiment of a collapsed cell culture system 1100 comprising a flexible portion 1102 and a mixing element 1104. The mixing element may comprise a foldable portion 1106, first and second suspension elements 1108, 1110, at least one hub 1112, and at least one arm. In various embodiments, the collapsed configuration of the cell culture system 1100 may result in the foldable portion 1106 folding to create a fold 1116 wherein the fold 1116 includes a fold angle 1118.

In various embodiments, the cell culture system 1100 may be collapsed to a substantially collapsed configuration. In a collapsed configuration the mixing element 1104 may fold to a substantially flat configuration and the flexible portion 1102 may fold to a substantially flat configuration. In some embodiments, the amount of collapsibility may be restricted by the rigid materials of the system such as the suspension elements 1108, 1110. Such a configuration allows for smaller packaging during shipping and when the cell culture system 1100 arrives to an end user they may inflate the cell culture system 1100 into an operational configuration. Additionally, when the cell culture system 1100 has been used and is ready for disposal it may be deflated to reduce a waste footprint. Inflation and deflation may occur through a port in the flexible portion.

In various embodiments, the mixing element 1104 may include a foldable portion 1106 configured to create a fold 1116 having a fold angle 1118 as the cell culture system 1100 collapses. In various embodiments the fold angle may be about 0 degrees to about 179 degrees, about 0 degrees to about 90 degrees, about 0 degrees to about 80 degrees, about 0 degrees to about 70 degrees, about 0 degrees to about 60 degrees, about 0 degrees to about 50 degrees, about 0 degrees to about 40 degrees, about 0 degrees to about 30 degrees, about 0 degrees to about 20 degrees, about 0 degrees to about 10 degrees, or about 0 degrees to about 5 degrees.

In various embodiments, the flexible portion 1102 may be configured to collapse to about 15%, about 10%, about 5%, about 10% to about 20%, about 5% to about 25%, about 5% to about 10%, about 15% to about 20%, about 20% to about 25% its operational configuration or inflated volume. In various embodiments, inflation and deflation may be facilitated though a port within the flexible portion 1102 using a compressed gas source.

Figure 12:
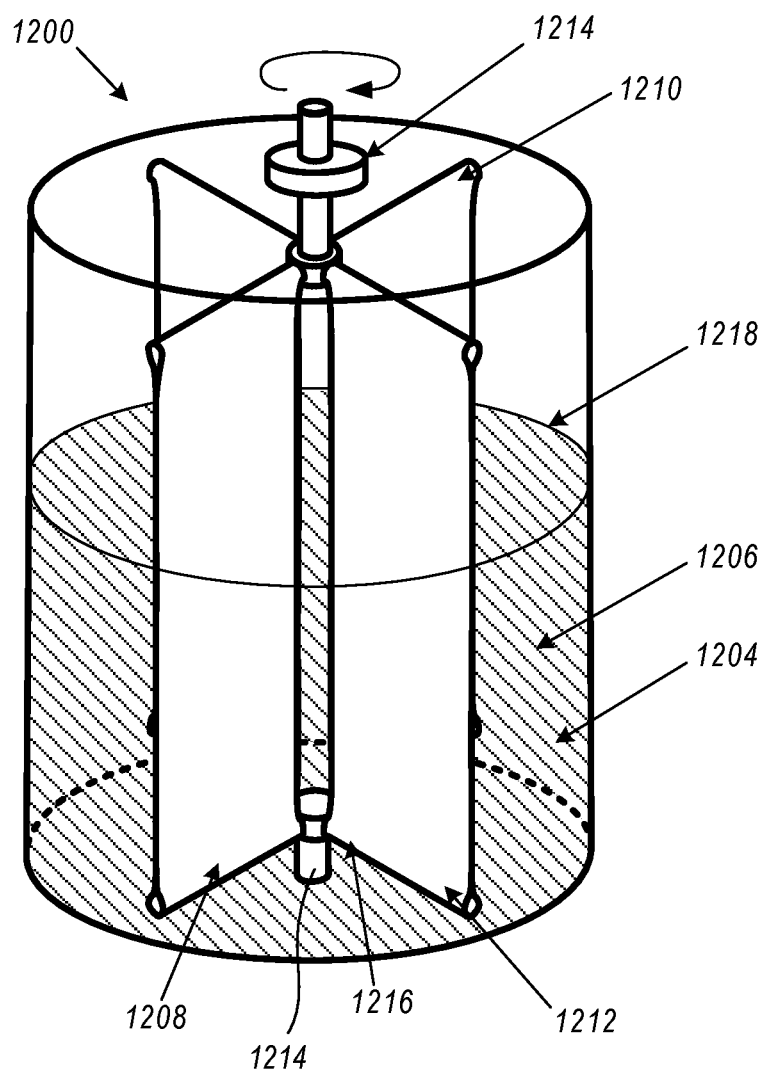
FIG. 12 illustrates a perspective view of another exemplary cell culture system according to one of the various embodiments.

FIG. 12 is an illustration of an embodiment of a cell culture system 1200 comprising a flexible portion 1202 configured to contain a cell culture 1206 with a cell culture level 1218 and a mixing element 1204. In various embodiments, the mixing element 1204 may include a foldable portion 1208, first and second suspension elements 1210, 1212, at least one hub 1214, and at least one arm 1216.

In various embodiments, a hub 1214 may be in physical communication with one or more arms 1216. In some embodiments, the hub 1214 may be in physical communication with one, two, three, or four arms 1216. In some embodiments, the hub 1214 and arms 1216 may have an opposing hub 1214 and arms 1216 located on the opposite side of the flexible portion 1202. In some embodiments, one or both hubs 1214 may be partially disposed to the exterior of the flexible portion 1202 through a sterile interface. Additionally, one of both of the hubs 1214 may be connected to a drive apparatus. In some embodiments, a foldable portion extends between opposing arms 1216. The embodiment shown in FIG. 12 depicts each hub 1214 being connected to four arms 1216 and four foldable portions 1208 may be suspended there between. However, any number of arms 1216 may be in physical communication with each of the hubs 1214 to support any number of foldable portions 1208.

In various embodiments, the cell culture 1206 may comprise cells, nutrients, and dissolved gases. In some embodiments, the dissolved gases may include oxygen, carbon dioxide, or nitrogen. In other embodiments, the cell culture 1206 may comprise anything assisting cellular function or cellular growth. In some embodiments, the cell culture level 1218 stays below the highest point of the foldable portion 1208 or mixing element 1204. In such embodiments, this may be due to the mixing element 1208 spanning nearly the entire height of the flexible portion 1202.

Figure 13:
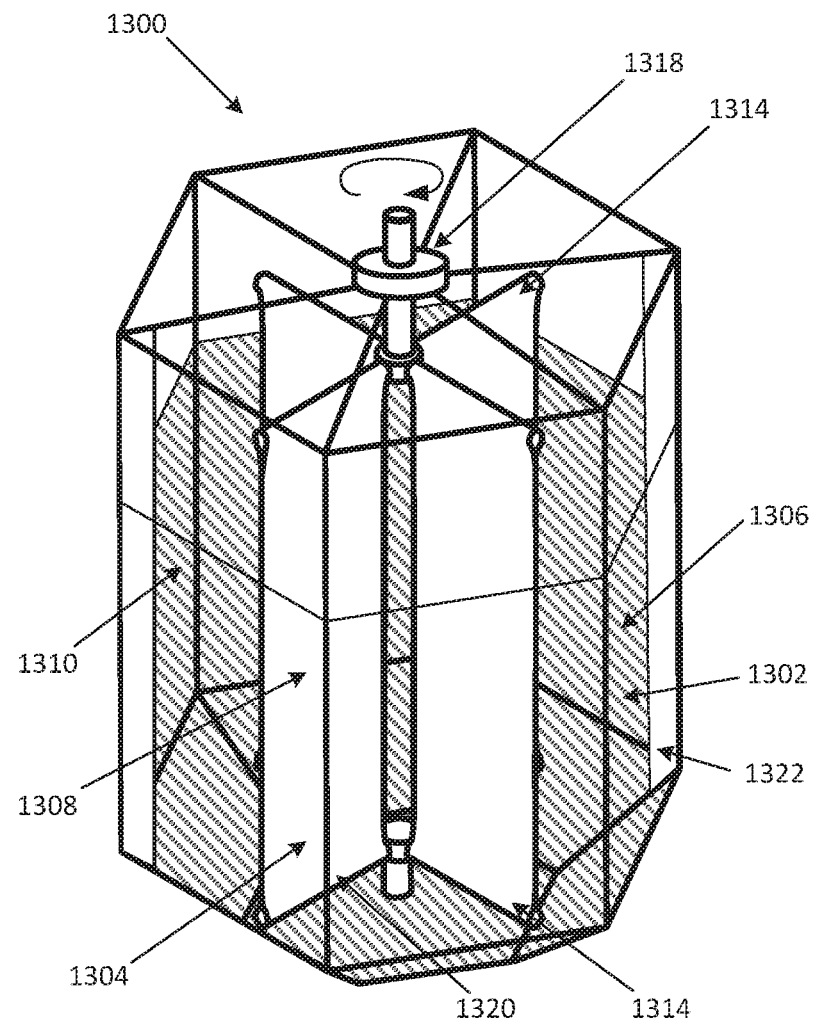
FIG. 13 illustrates a perspective view of another exemplary cell culture system according to one of the various embodiments.

FIG. 13 is an illustration of an embodiment of a cell culture system 1300 comprising a flexible portion 1302 and a mixing element 1304. In various embodiments, the flexible portion 1302 may include a cell culture 1306, one or more panels 1310, one or more seams 1312, and a baffle 1322. In various embodiments the mixing element may include a foldable portion 1308, first and second suspension elements 1314, 1316, one or more hubs 1318, and one or more arms 1320.

In various embodiments, the flexible portion 1302 may include a cylindrical, elliptical, or polygonal shape or cross-section. In some embodiments, the flexible portion 1302 may include a trigon, tetragon, pentagon, hexagon, heptagon, octagon, nonagon, or decagon shape with corresponding cross-section.

In various embodiments, a baffle 1322 may be affixed to the interior surface of the flexible portion 1302. In some embodiments, a baffle may include a surface feature welded, adhered, a mechanical attachment. In other embodiments, a polygonal shaped flexible portion 1302 may act as baffle by continuously changing the distance between the mixing element and the side wall of the flexible portion 1302 while the cell culture system 1300 is in operation.

In various embodiments, four or more panels 1310 may be joined by seams 1312 to create a flexible portion 1302. In some embodiments, the flexible portion 1302 may include a single polymeric sheet and the seams 1312 may include a fold. In other embodiments, each panel 1310 may be a separate piece of polymeric sheet and the seams 1312 may be joined using a weld or adhesive.

Figure 14:
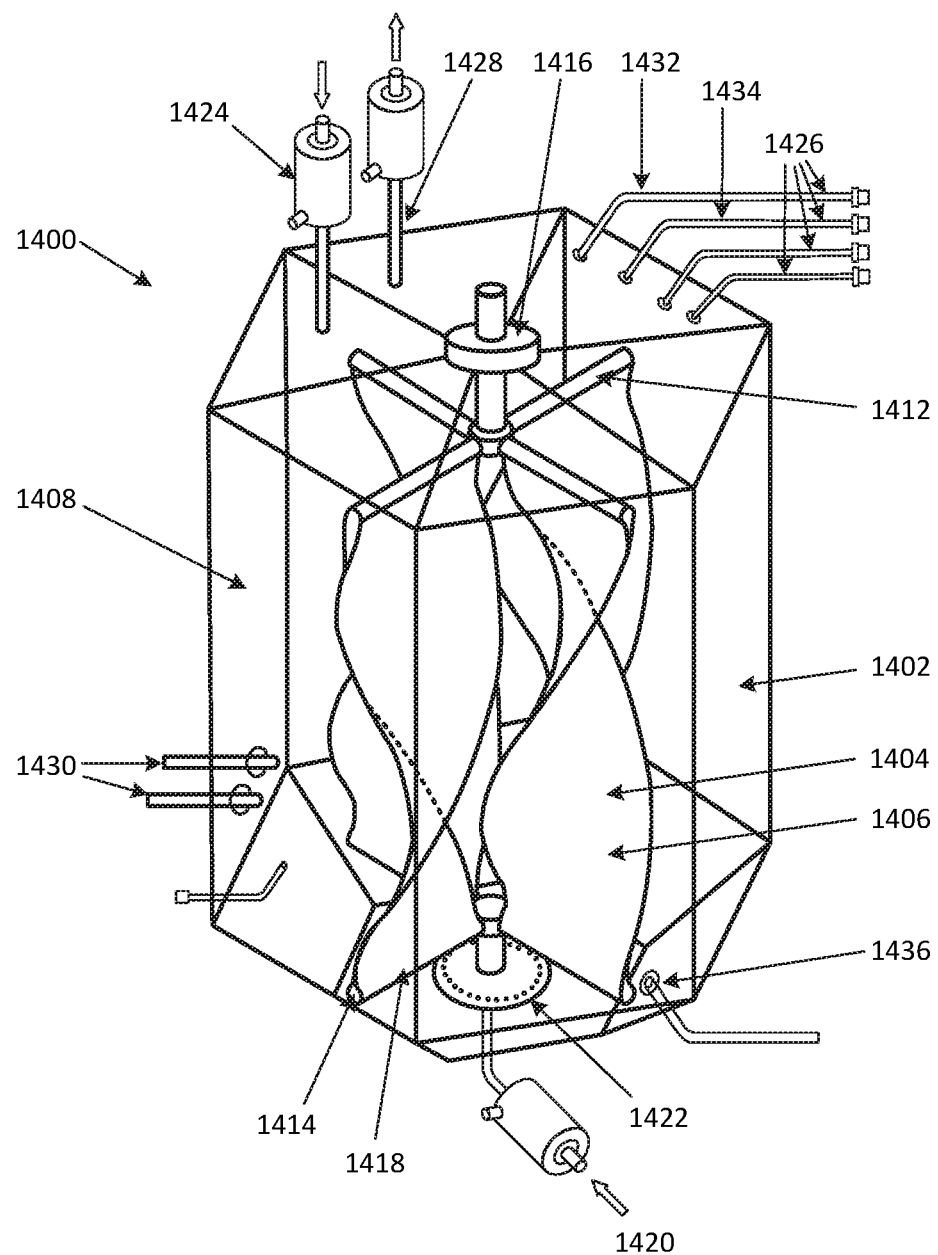
FIG. 14 illustrates a perspective view of another exemplary cell culture system including peripherals according to one of the various embodiments.

FIG. 14 is an illustration of an embodiment of a cell culture system 1400 comprising a flexible portion 1402 and a mixing element 1404. In various embodiments, the mixing element may include a foldable portion 1406, first and second suspension elements 1412, 1414, at least one hub 1416, and at least one arm 1418. In various embodiments, the flexible portion may include four or more panels 1408, seams 1410, one or more sterile gas inlets 1420, one or more spargers 1422, one or more filter elements 1424, one or more ports 1426, a gas outlet 1428, and a baffle 1436. In some embodiments, ports may include at least one sensor port 1430, at least one sampling port 1432, and at least one tube port 1434 located either above the liquid surface or below the liquid surface 1436.

In various embodiments, the foldable portion 1406 may be twisted one or more times to increase turbulent fluid flow. In some embodiments, such a configuration may reduce uniformity of fluid flow, thereby increasing turbulent flow. In additional embodiments, the twisted configuration may reduce the interaction of the cell culture with the foldable portion 1406. In other embodiments, the twisted foldable portion 1406 may act like a channel to direct fluid flow.

In various embodiments, a cell culture may be aerated using either the mixing element 1404, the sparger 1422, or both in conjunction with one another. In some embodiments, the sparger may be a ring sparger or a cross-flow sparger. In some embodiments, the sparger 1422 may be in communication with a compressed gas source through a sterile port 1426. In some embodiments, aeration may remove unwanted carbon dioxide while increasing the amount of dissolved oxygen.

In various embodiments, the ports 1426 used for gas or liquid exchange may include filter elements 1424. In some embodiments, one or more sterile gas inlets 1420 may include one or more filter elements 1424. In some embodiments, one or more sterile gas outlets 1428 may include one or more filter elements 1424.

In various embodiments, there may be one or more sensor ports 1430 configured to receive an electrochemical probe, an optical probe, or both.

In various embodiments, the contents of the cell culture system 1400 may be harvested though one of the ports 1430. In some embodiments, the contents of the cell culture system 1400 may be harvested though the sampling port 1432, tube port 1434, or both. In various embodiments, the contents being harvested from a cell culture may include cells, proteins, enzymes, biosimilars, or anything that may be grown in a cell culture. In various embodiments, tubing may be secured to the ports 1430 of the flexible portion 1402.

Figure 15:
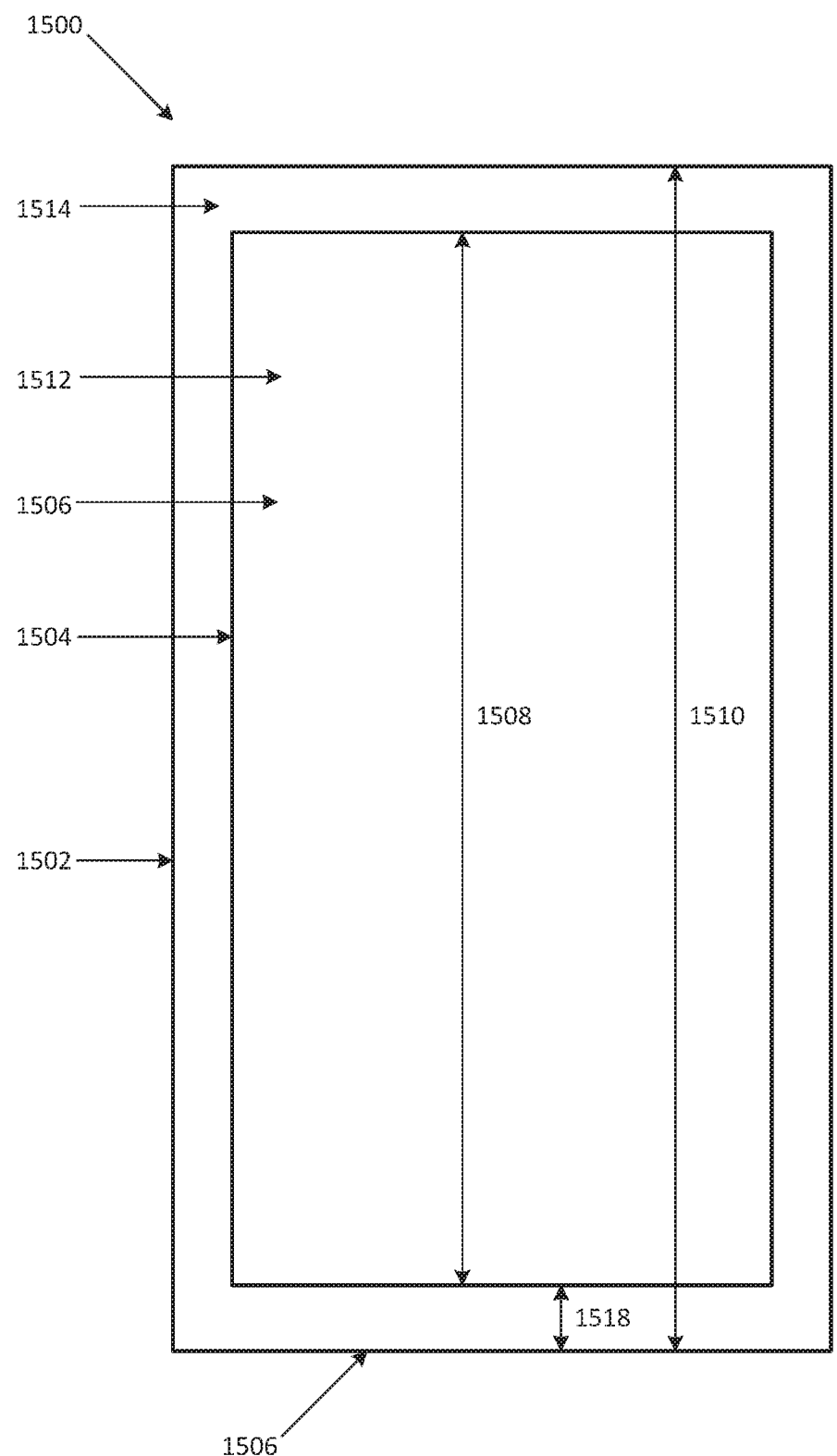
FIG. 15 illustrates a cross-sectional view of an exemplary cell culture system depicting a flexible portion and a mixing element according to one of the various embodiments.

FIG. 15 is a cross-sectional view of an embodiment of a cell culture system 1500 comprising a flexible portion 1502 having a surface and a mixing element 1504. In various embodiments, the mixing element 1504 may include a foldable portion 1506 having a foldable portion height 1508 and the flexible portion 1502 may have a flexible portion height. In some embodiments, the foldable portion 1504 may have a cross-sectional area and the flexible portion may have a cross-sectional area. In some embodiments a space 1518 may be included between the surface 1516 of the flexible portion and the foldable portion 1504.

In various embodiments, the space 1518 may define a minimal working volume. A minimal working volume means the lowest fluid volume that still allows the mixing element 1504 or foldable portion 1508 to still be in physical contact with a cell culture. In various embodiments, the minimal working volume may be about 1% to about 20%, about 5% to about 15%, about 7% to about 12%, about 1% to about 5%, about 5% to about 10%, about 10% to about 15%, about 15% to about 20%.

In various embodiments, a sweep area ratio may be defined as the largest cross-sectional surface area of the mixing element 1504 or foldable portion 1506 divided by the largest cross-sectional area of the flexible portion 1502. In some embodiments, a sweep area ratio may be defined as a cross-sectional surface area of the mixing element 1504 or foldable portion 1506 divided by the cross-section area of the flexible portion 1502. In the later embodiment, the flexible portion may not be circular so the sweep area ratio may change while the cell culture system 1500 is in operation.

In various embodiments, the sweep area ratio may be about 0.25 to about 1.0, about 0.5 to about 1.0, about 0.75 to about 1.0, about 0.25 to about 0.35, about 0.35 to about 0.45, about 0.45 to about 0.55, about 0.55 to about 0.65, about 0.65 to about 0.75, about 0.75 to about 0.85, about 0.85 to about 0.95, or about 0.95 to about 1.0.

In various embodiments, the foldable portion height 1508 compared to the flexible portion height 1508 may be about 0.5 to about 1.0, about 0.7 to about 0.95, about 0.8 to about 0.9, about 0.8, about 0.9, or about 0.95.

Figure 16:
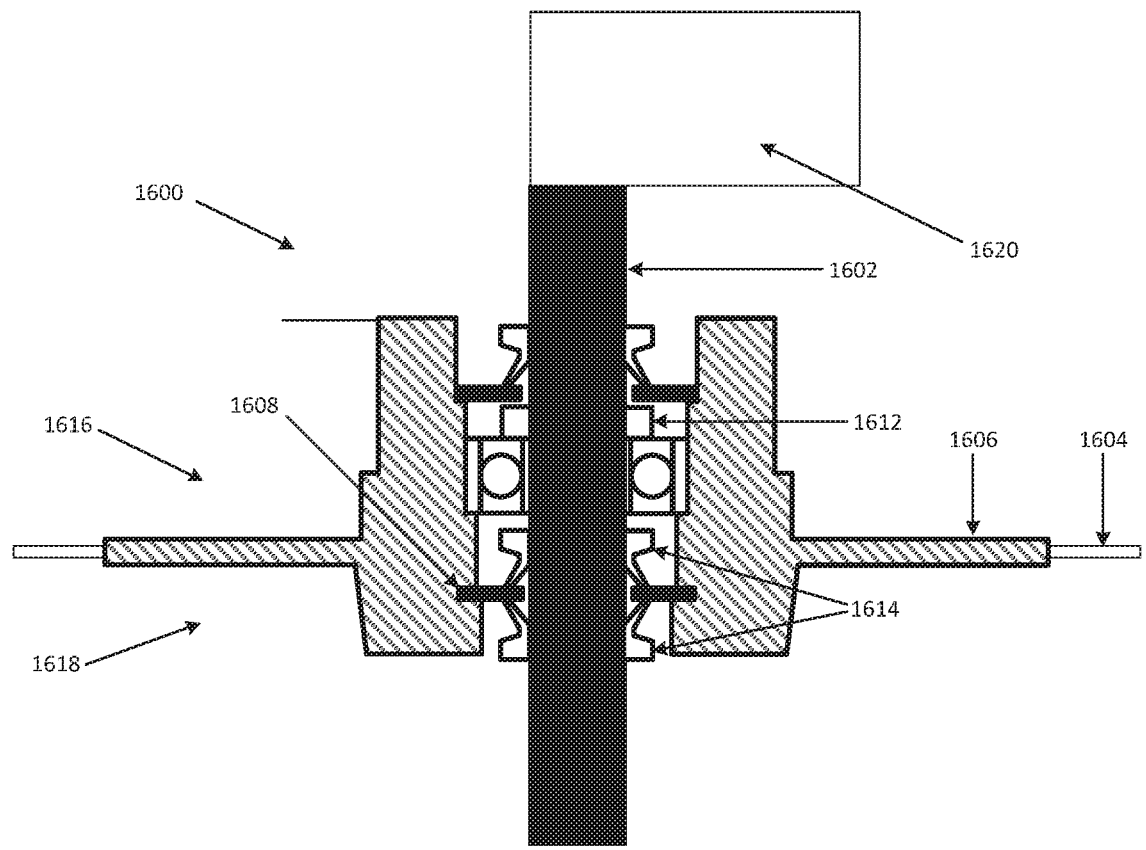
FIG. 16 illustrates a cross-sectional view of an exemplary mechanically driven rotor assembly according to one of the various embodiments.

FIG. 16 illustrates an embodiment of a rotor assembly 1600 comprising a hub 1602, a housing 1606, one or more seals 1614, one or more ball bearings 1610, one or more washers 1608, and one or more snap rings 1612. In some embodiments, the housing 1606 seals to the flexible portion 1604 with a weld or adhesive. In various embodiments, the flexible portion 1604 separates a sterile interior portion 1616 from an exterior portion 1618. In other embodiments, the housing 1606 may fit into a port in order to create a sterile seal. In such an embodiment, a weld, adhesive, mechanical seal or a combination may be used.

In various embodiments, the rotor assembly 1600 may allow a hub 1602 to communicate with both an interior portion 1618 and an exterior portion 1616. The portion of the hub 1602 communicating with the exterior may interact with a drive 1620 to rotate a mixing element disposed within the flexible portion 1604.

In various embodiments, the one or more ball bearings 1610 may be configured to provide rotational movement to the hub 1602. In some embodiments, the ball bearings may be constructed from single use materials such as USP class VI materials. In various embodiments, the one or more seals 1614 may be configured to ensure sterility within the interior portion 1616 of the flexible portion 1604. In other embodiments, the one or more washers 1608 may ensure the one or more ball bearings 1610 may be positioned correctly within the housing 1606. In addition embodiments, the one or more snap rings 1612 support the mechanical alignment of the one or more ball bearings 1610 within the rotor assembly 1600.

Figure 17:
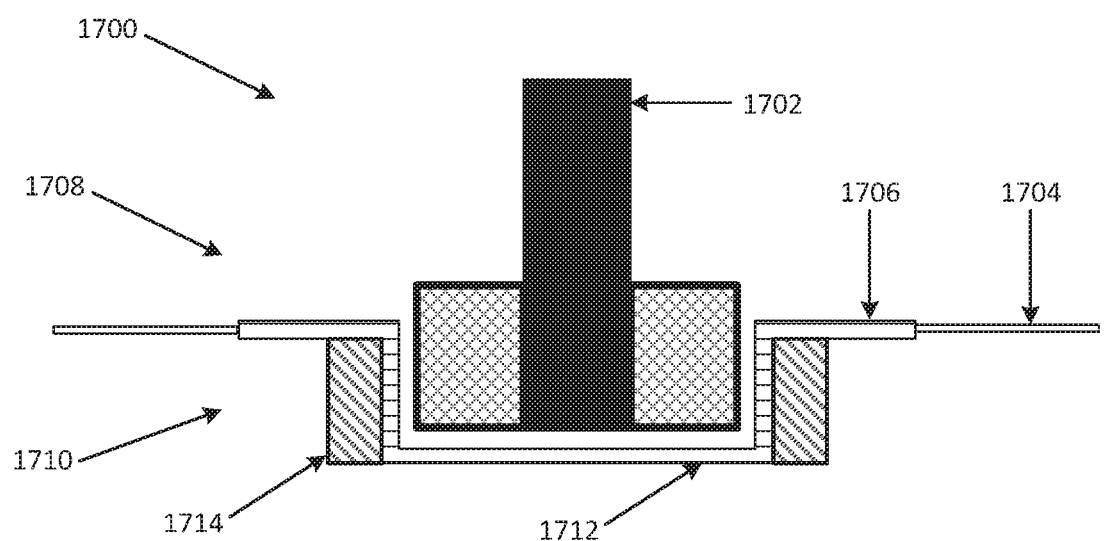
FIG. 17 illustrates a cross-sectional view of an exemplary magnetically driven rotor assembly according to one of the various embodiments.

FIG. 17 illustrates an embodiment of a rotor assembly 1700 comprising a hub 1702, a housing 1706, a positioning cage 1712, and one or more magnets 1714. In some embodiments, the housing 1706 may seal to the flexible portion 1704 with a weld or adhesive. In various embodiments, the flexible portion 1704 may separate a sterile interior portion 1708 from an exterior portion 1710.

In various embodiments, there may be no need to create a seal because communication between an interior portion 1708 and an exterior portion 1710 may not be required for a magnetically driven mixing element. In some embodiments, two opposing magnets 1714 may be positioned on the exterior of the positioning cage 1712 where they may be in electromagnetic magnetic communication with the hub 1702 contained within the flexible portion 1704. In some embodiments, the hub 1702 may be prevented from leaving the positioning cage 1712 with a physical barrier that does not prevent rotational movement. In various embodiments, the hub may comprise a metal having magnetic properties such as iron, nickel, or cobalt or comprise an electromagnet.

Figure 1:
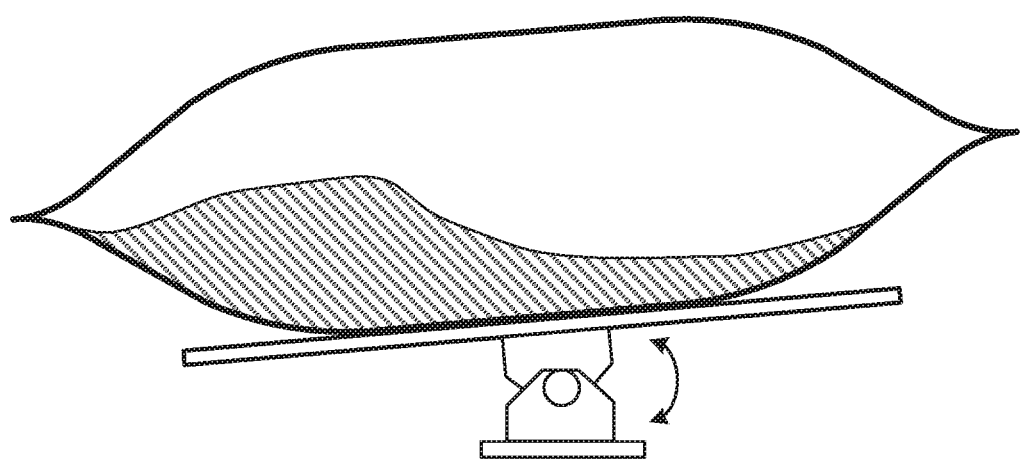
FIG. 1 illustrates a side view of a wave style bioreactor according to the prior art.
Figure 2:
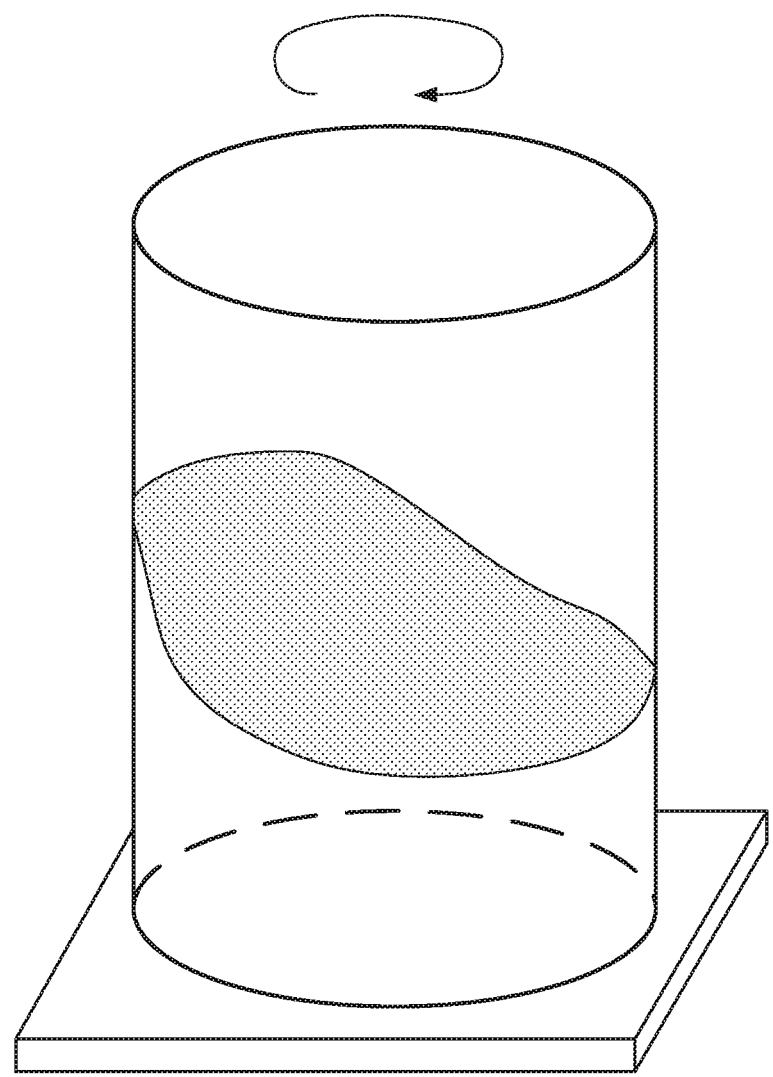
FIG. 2 illustrates a front perspective view of an orbital style bioreactor according to the prior art.
Figure 3:
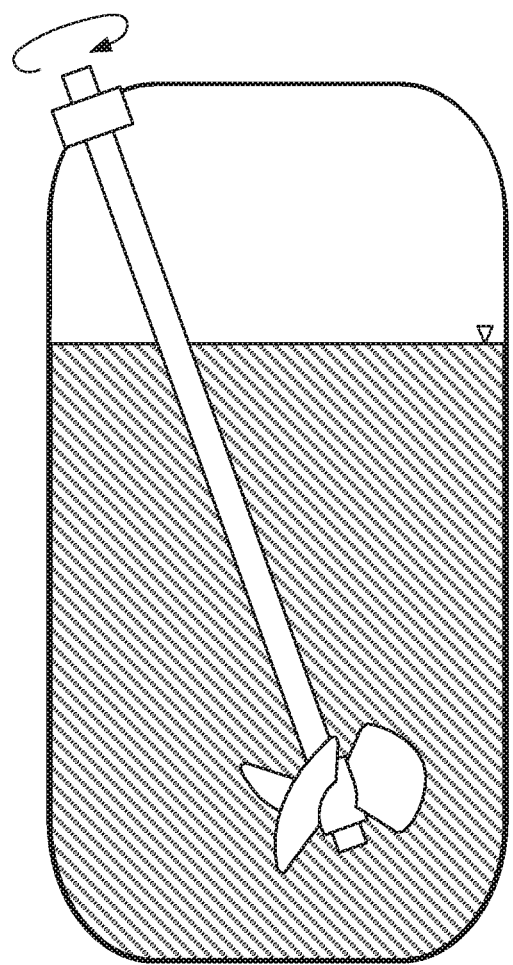
FIG. 3 illustrates a front view of a stirred-tank bioreactor having a single impeller according to the prior art.
Figure 4:
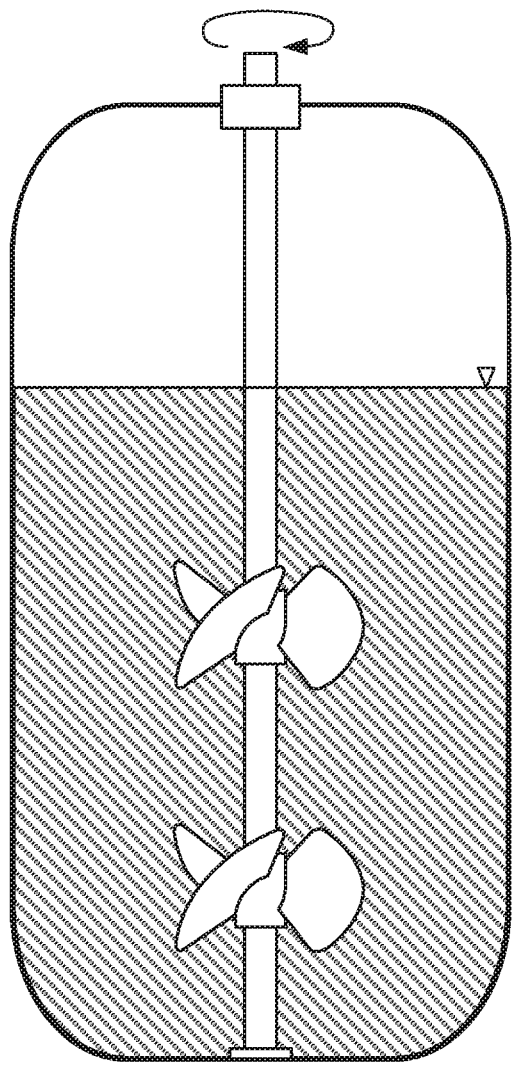
FIG. 4 illustrates a front view of a stirred-tank bioreactor having multiple impellers according to the prior art.
Figure 18:
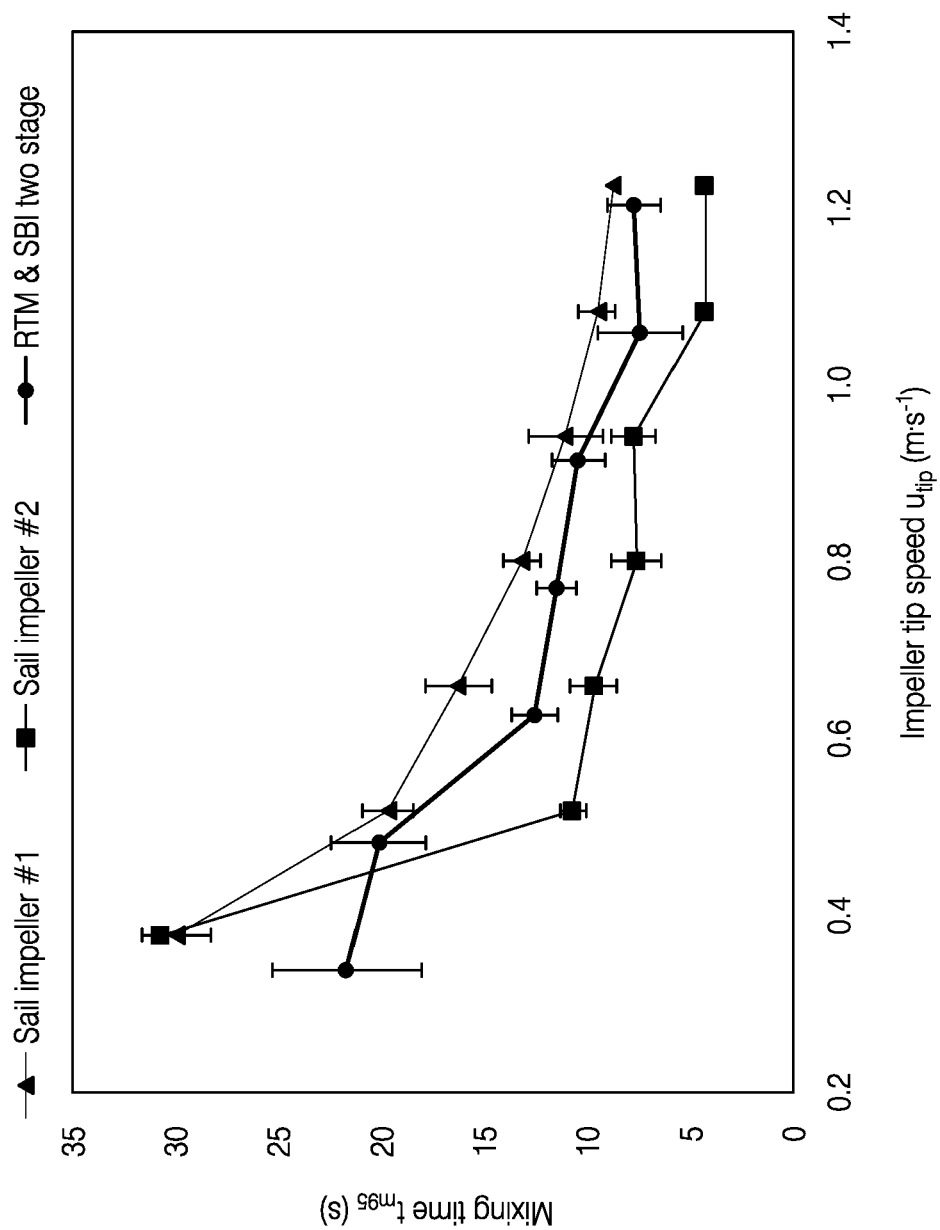
FIG. 18 illustrates a graph showing experimentally determined mixing times for two exemplary cell culture systems.

FIG. 18 illustrates experimental data including measured mixing times on the y-axis and impeller tip speed on the x-axis. In this illustration, two prototypes were compared to a conventional glass bioreactor. Both the prototypes and conventional bioreactors used a 10 L working volume during the test. The conventional bioreactor included a two stage conventional impeller (see FIG. 4). The sail impeller #1 used a four, straight sail design (see FIG. 13). The sail impeller #2 used a four, twisted sail design (see FIG. 14). A conductivity based sensor method was used to determine the mixing time for 95% homogenization. The experiments were conducted at least four times for each impeller speed and the results in FIG. 18 include the mean values and simple standard deviation (n=4). The mixing times for the sail impellers decreased from about 30 seconds to between about 5 seconds and 10 seconds with increasing impeller speeds ($u_{tip}=\pi*d*N$). Shorter mixing times were obtained using the twisted sail impeller as compared to both the conventional bioreactor and the straight sail impeller. However, both sail impellers demonstrated shorter mixing times than when compared to the conventional two stage impeller bioreactor for impeller tip speeds above 0.5 $m*s^{-1}$. This result is due to the higher output that results from the large momentum transfer surface area and the larger swept volume of the prototypes. Furthermore, a higher turbulence is also expected at a given tip speed, based on the impeller Reynolds number ($Re=N*d^2/v$), due to the larger diameter of the sail impellers, even though the impeller speed is lower for a given impeller tip speed ($u_{tip}=\pi*N*d$).

Figure 19:
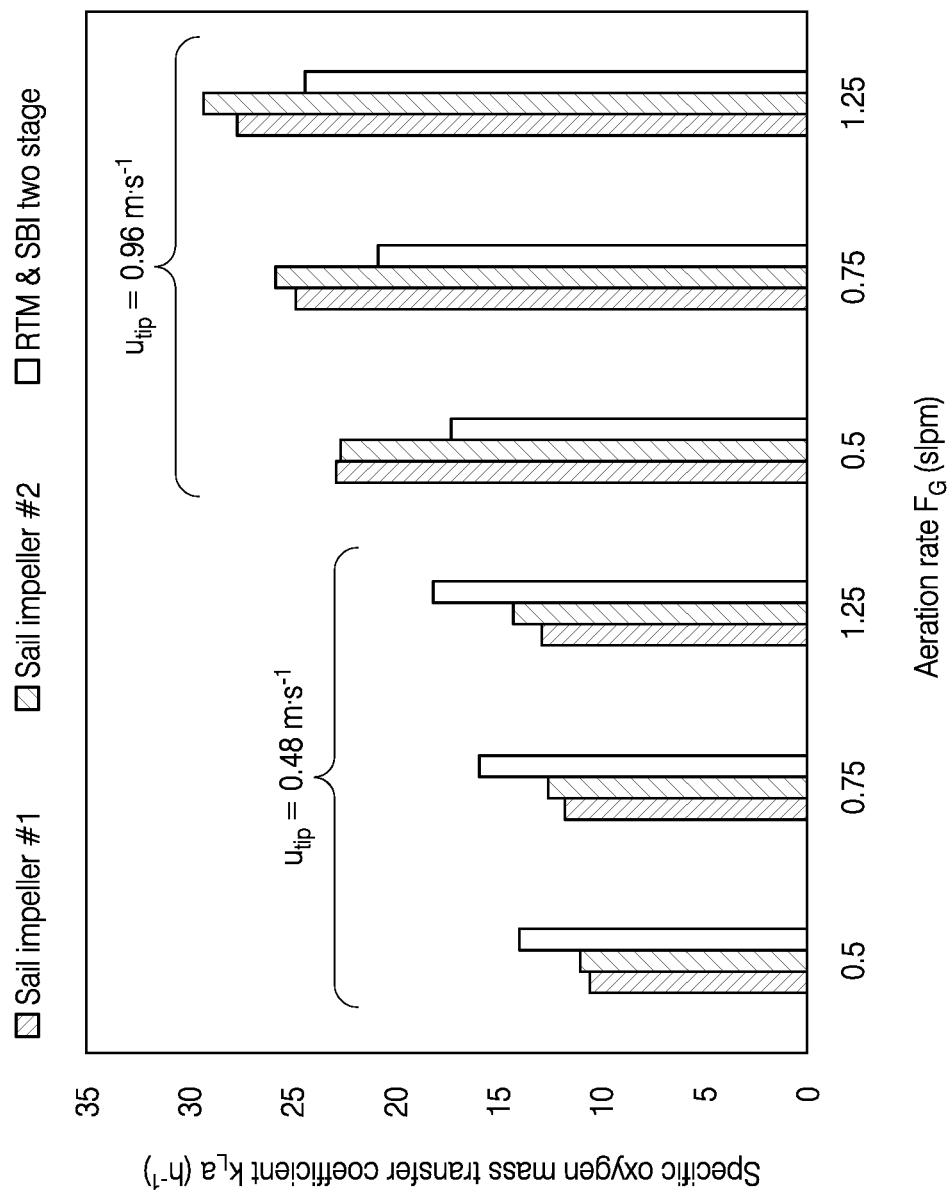
FIG. 19 illustrates a bar chart showing experimentally determined specific oxygen mass transfer coefficients for two exemplary cell culture systems.

FIG. 19 illustrates experimental data including specific oxygen mass transfer coefficients ($k_L a$) using the same prototypes and conventional bioreactor as a reference. The $k_L a$ value determines the rate of oxygen mass transfer from the gas to the liquid phase for a giving oxygen concentration gradient ($OTR=k_L a*\Delta c$). The gas mass transfer rate was estimated for two agitation speeds as a function of the aeration rate using the dynamic gassing out method standard in the field. Gas was introduced into the bioreactors via a sparger mounted below the lower sail holder or the lower impeller respectively. The sizes of the sparger holes were comparable in all vessels in order to guarantee similar initial bubble sizes and thus similar volumetric gas-liquid interface surfaces areas. As depicted in FIG. 19, the $k_L a$ values increased with increasing aeration rates and agitator tip speeds and were between 10 $h^{-1}$ and 30 $h^{-1}$ which is sufficient for medium to high cell densities of low to medium oxygen demanding cell cultures. The twisted sail configuration (design #2) had higher $k_L a$ values than the straight sails (design #1), irrespective of the agitation and aeration parameters. This may be explained by the improved mixing and gas dispersion observed during the experiment.

Figure 20:
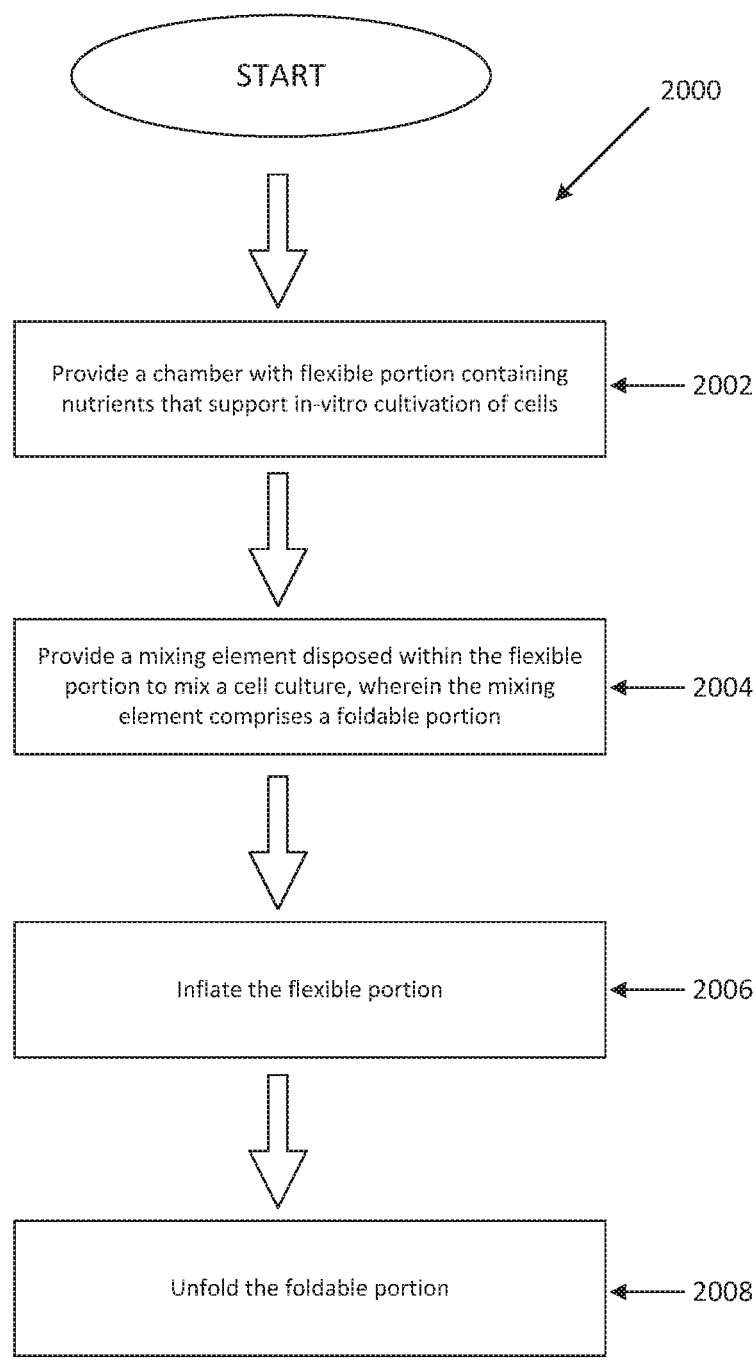
FIG. 20 illustrates a flow diagram according to one of the various embodiments.

FIG. 20 illustrates an exemplary flowchart showing a method 2000 for culturing cells in accordance with various embodiments. In step 2002, a flexible portion containing nutrients to support in vitro cultivation of a cell may be provided. In step 2004, a mixing element disposed within the flexible portion to mix a cell culture, wherein the mixing element comprises a foldable portion may be provided. In step 2006, the flexible portion may be inflated. In step 2008, the foldable portion may be unfolded.

In various embodiments, the method may include the step of cells being added to the cell culture. In other embodiments, the method may include the step of cells being cultured. In some embodiments, the method may include the step of harvesting a component of the cell culture. In various embodiments, the method may include the step of mixing a fluid comprising a cell culture using a mixing element.

In various embodiments, the method may include the step of collapsing the flexible portion to about 15%, about 10%, about 5%, about 10% to about 20%, about 5% to about 25%, about 5% to about 10%, about 15% to about 20%, or about 20% to about 25% of its operation configuration.

Figure 21:
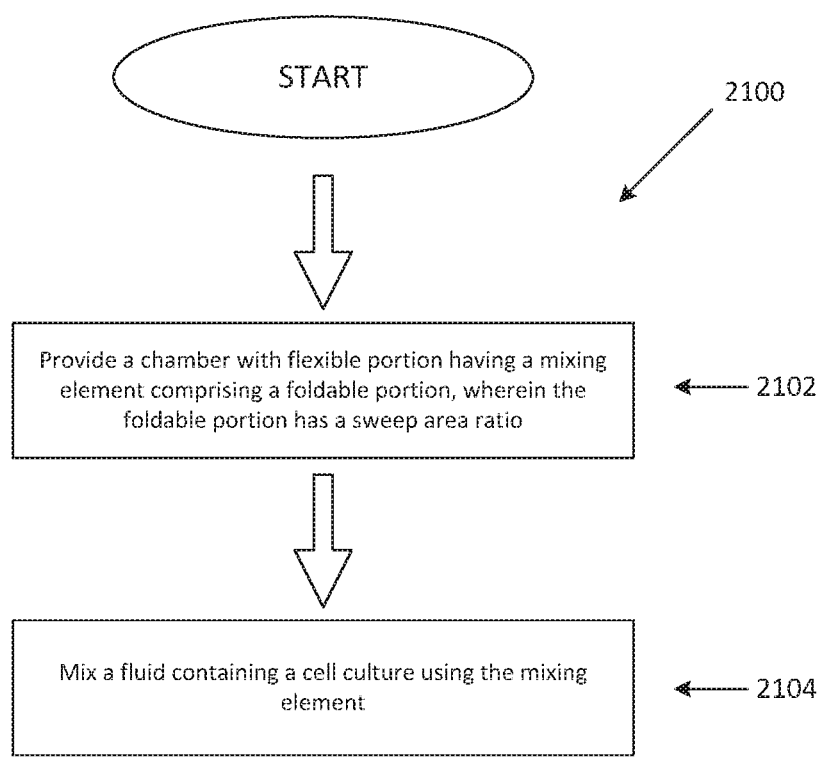
FIG. 21 illustrates a flow diagram according to one of the various embodiments.

FIG. 21 illustrates an exemplary flowchart showing a method 2100 for culturing cells and reducing cellular shear stress in accordance with various embodiments. In step 2102, a flexible portion having a mixing element comprising a foldable portion and the foldable portion has a sweep area ratio is provided. In step 2104, a fluid containing a cell culture may be mixed using a mixing element.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art will readily appreciate that the sequences may be varied and still remain within the spirit and scope of the various embodiments.

The invention claimed is:

1. A collapsible cell culture vessel, comprising:
   a flexible portion comprising a collapsible container bounding a chamber that is adapted to support a cell culture; and
   a mixing element disposed within the collapsible container, the mixing element comprising:
   a first suspension element rotatably disposed within the chamber of the collapsible container;
   a second suspension element rotatably disposed within the chamber of the collapsible container, the second suspension element being spaced apart from the first suspension element;
   one or more foldable portions each extending between a first end and an opposing second end, the first end being connected to the first suspension element and the second end being connected to the second suspension element, each of the one or more foldable portions comprising a flexible sheet having a front face and an opposing back face that both extend between the first end and the opposing second end; and a surface feature outwardly projecting from the front face of the flexible sheet of each of the one or more foldable portions.

2. The cell culture vessel of claim 1, wherein each of the one or more foldable portions folds substantially flat when the flexible portion is collapsed.

3. The cell culture vessel of claim 1, wherein the flexible sheet comprises a polymeric sheet.

4. The cell culture vessel of claim 1, wherein the flexible sheet is substantially rectangular.

5. The cell culture vessel of claim 1, further comprising an opening extending through the flexible sheet between the front face and the opposing back face.

6. The cell culture vessel of claim 1, further comprising:
the first suspension element comprising a first hub rotatably disposed within the collapsible container and a first arm projecting from the first hub;
the second suspension element comprising a second hub rotatably disposed within the collapsible container and a first arm projecting from the second hub; and
the one or more foldable portions comprising a first foldable portion extending between the first arm of the first suspension element and the first arm of the second suspension element, the first foldable portion comprising a first flexible sheet having the front face and the opposing back face.

7. The cell culture vessel of claim 6, wherein a portion of the first hub is in physical communication to an exterior of the collapsible container through a rotor assembly.

8. The cell culture vessel of claim 6, wherein the first arm of the first suspension element is configured to telescope between two lengths.

9. The cell culture vessel of claim 6, further comprising:
a second arm projecting from the first hub;
a second arm projecting from the second hub; and
the one or more foldable portions comprising a second foldable portion extending between the second arms, the second foldable portion comprising a second flexible sheet having the front face and the opposing back face.

10. The cell culture vessel of claim 6, further comprises a securing element joining the first foldable portion to the first arm projecting from the first hub.

11. The cell culture vessel of claim 1, wherein a sweep area ratio comprises a largest cross sectional area of the one or more foldable portion divided by a largest cross sectional area of the flexible portion, the sweep area ratio being about 0.25 to about 1.0.

12. The cell culture vessel of claim 1, wherein a space between an inner surface of the collapsible container and the one or more foldable portions determines a minimal working volume, the minimal working volume comprising between about 1% to about 20% of a total volume of the chamber of the collapsible container.

13. The culture vessel of claim 1, wherein the flexible sheet can be folded over an angle between about 90 degrees and about 179 degrees.

14. A collapsible cell culture vessel, comprising:
a collapsible container bounding a chamber adapted to support a cell culture; and
a mixing element disposed within the collapsible container, the mixing element comprising:
a first suspension element disposed within the chamber of the collapsible container, the first suspension element comprising a first hub rotatably disposed within the chamber of the collapsible container and a first arm projecting from the first hub;
a second suspension element disposed within the chamber of the collapsible container, the second suspension element comprising a second hub rotatably disposed within the chamber of the collapsible container and a first arm projecting from the second hub;
one or more foldable portions each extending between the first suspension element and the second suspension element and each comprising a flexible sheet having a front face and an opposing back face, the one or more foldable portions comprising a first flexible sheet having the front face and the opposing back face that extend between the first arm projecting from the first hub and the first arm projecting from the second hub, the first flexible sheet being sufficiently flexible that it can be folded over an angle between about 90 degrees and about 179 degrees; and
a surface feature outwardly projecting from the front face of the flexible sheet of each of the one or more foldable portions.

15. A method of culturing cells, comprising:
delivering a cell culture into a collapsible container; and
mixing the cell culture within collapsible container using
a mixing element disposed within the collapsible container, the mixing element comprising:
a first suspension element rotatably disposed within the collapsible container;
a second suspension element rotatably disposed within the collapsible container;
a first foldable portion extending between a first end and an opposing second end, the first end being connected to the first suspension element and the second end being connected to the second suspension element, the first foldable portion comprising a flexible first sheet having a front face and an opposing back face that both extend between the first end and the opposing second end; and
a surface feature outwardly projecting from the front face of the flexible first sheet.

16. The cell culture vessel of claim 1, wherein the first suspension element and the second suspension element are spaced apart within the chamber so that there is no direct or indirect connection between the first suspension element and the second suspension element within the chamber except through the one or more foldable portions.

17. The cell culture vessel of claim 14, wherein the first suspension element and the second suspension element are spaced apart within the chamber so that there is no direct or indirect connection between the first suspension element and the second suspension within the chamber except through the one or more foldable portions.

* * * * *